United States Patent
Hosaka et al.

(10) Patent No.: US 7,404,953 B2
(45) Date of Patent: Jul. 29, 2008

(54) METHODS USING EOSINOPHIL-SPECIFIC APOPTOSIS INDUCER

(75) Inventors: Emi Hosaka, Tokyo (JP); Kazuyasu Nakamura, Tokyo (JP); Masamichi Koike, Tokyo (JP); Kenya Shitara, Tokyo (JP); Nobuo Hanai, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 554 days.

(21) Appl. No.: 10/204,326

(22) PCT Filed: Feb. 15, 2001

(86) PCT No.: PCT/JP01/01077

§ 371 (c)(1),
(2), (4) Date: Dec. 23, 2002

(87) PCT Pub. No.: WO01/60405

PCT Pub. Date: Aug. 23, 2001

(65) Prior Publication Data

US 2004/0136996 A1 Jul. 15, 2004

(30) Foreign Application Priority Data

Feb. 15, 2000 (JP) .............................. 2000-036671

(51) Int. Cl.
*A61K 39/395* (2006.01)
(52) U.S. Cl. ................................. 424/130.1; 424/141.1
(58) Field of Classification Search ........................ None
See application file for complete search history.

(56) References Cited

U.S. PATENT DOCUMENTS

| 6,018,032 | A | 1/2000 | Koike et al. |
| 6,465,616 | B1 * | 10/2002 | Lopez et al. ................. 530/350 |
| 6,538,111 | B1 | 3/2003 | Koike et al. |
| 7,179,464 | B2 | 2/2007 | Koike et al. |
| 7,238,354 | B2 | 7/2007 | Koike et al. |
| 2007/0048304 | A1 | 3/2007 | Koike et al. |

FOREIGN PATENT DOCUMENTS

| WO | WO 98/47923 | 10/1997 |
| WO | WO 97/48418 | 12/1997 |

OTHER PUBLICATIONS

H. Yasumichi et al., Int. Immunol., vol. 3, No. 2, pp. 135-139 (1991).
K. Takatsu et al., Zouketsu Inshi, vol. 2, No. 3, pp. 71-80 (1991) & English Translation of the related portion.
H-U Simon, et al., J. Immunol. pp. 3902-3908 (1997).
A.F. Lopez et al., J. Exp. Med., vol. 167, pp. 219-224 (1988).
M. Migita et al., Cell. Immunol., vol. 133, pp. 484-497 (1991).
M.E. Rothenberg et al., J. Immunol., vol. 143, pp. 2311-2316 (1989).
C.J. Sanderson, Blood, vol. 79, No. 12, pp. 3101-3109 (1992).
Simon H.U. Eosinophil apoptosis in allergic diseases—an emerging new issue. Clin Exp Allergy. Nov. 1998;28(11):1321-4.

* cited by examiner

*Primary Examiner*—Michael Pak
(74) *Attorney, Agent, or Firm*—Fitzpatrick, Cella, Harper & Scinto

(57) ABSTRACT

The present invention provides an apoptosis inducer and a therapeutic agent for eosinophilic diseases which comprises, as an active ingredient, an antibody which reacts specifically with eosinophils and induces apoptosis of eosinophils; and a method for inducing eosinophil apoptosis using the antibody, and a method for specifically reducing or removing eosinophils in peripheral blood or tissues using the antibody.

12 Claims, 11 Drawing Sheets

METHODS USING EOSINOPHIL-SPECIFIC APOPTOSIS INDUCER

This is the national stage under 37 CFR §3.71 of International Application No. PCT/JP01/01077 filed Feb. 15, 2001 which in turn claims priority of Japanese application number 2000-036671 filed on Feb. 15, 2000.

TECHNICAL FIELD

The present invention relates to an apoptosis inducer and a therapeutic agent for eosinophil associated diseases which comprises, as an active ingredient, an antibody which reacts specifically with eosinophils and induces apoptosis of eosinophils. The present invention also relates to a method for specifically inducing eosinophil apoptosis using the antibody, and a method for specifically reducing or removing eosinophils in peripheral blood or a tissue using the antibody.

BACKGROUND ART

Eosinophils are implicated in various diseases including allergic diseases, and are thought to play an important role in generating morbidity of allergic diseases such as chronic bronchial asthma and atopic dermatitis [Adv. Immunol., 39, 177(1986), Immunol. Today, 13, 501(1992)].

In addition to the above diseases, eosinophils are also implicated in diseases generally referred to as hypereosinophilic syndrome (HES), such as eosinophilia, eosinophilic enterogastritis, eosinophilic leukemia, eosinophilic granuloma and Kimura's disease [Ann. Intern. Med., 97, 78 (1982)].

Eosinophilic granuloma is nonneoplastic cryptogenic lesion, which is an osteolytic and focal, and is known to be associated with remarkable tissue cosinophulia [U.S. Armed Forces Med. J., 2, 1085 (1951)]. According to the registry of bone tumor patients in Japan (1972-1984), 379 out of 404 bone tumor patients (93.8%) suffered from eosinophilic granuloma. Hence, in addition to inflammatory diseases, such as allergy, eosinophils can cause other various diseases.

Interleukin-5 (hereinafter referred to as IL-5), interleukin-3 (hereinafter referred to as IL-3) and granulocyte-macrophage colony-stimulating factor (hereinafter referred to as GM-CSF), which are members of cytokine family, are involved in regulating the differentiation, proliferation and activation of eosinophils. Of these cytokines, IL-5 is known to act specifically on eosinophils and specifically induce the terminal differentiation [Proc. Natl. Acad. Sci. U.S.A., 85, 2288 (1988)].

An anti-IL-5 antibody has been developed as an anti-inflammatory agent. A humanized anti-IL-5 antibody, SB-240563 (Smithkline Beecham), is effective in reducing the number of eosinophils in peripheral blood of mild asthma patients (100th Annual Meetings of the American Society for Clinical Pharmacology and Therapeutics, March/1999). Moreover, a humanized anti-IL-5 antibody, Sch-55700 (CDP-835) (Scherring-Plough/Celltech) is known to inhibit lung eosinophilia induced by antigens in allergic monkey models [Arzneimittel-Forschung, 49, 779 (1999)].

In vitro, IL-3 and/or GM-CSF can activate eosinophils or prolong their survival [J. Clin. Invest., 81, 1986 (1988)]. Further, IL-3 and/or GM-CSF acts also predominantly on the induction of immature eosinophils from myeloid stem cells [Blood, 76, 1956 (1990)]. Furthermore, chemokines such as eotaxin and RANTES (regulated on activation normal T-cell expressed and secreted), induce the chemotaxis of eosinophils to inflamed site [Clin. Exp. Allergy, 26, 1005 (1996)].

Stem cell factors (hereinafter referred to as SCF) are involved in the accumulation of eosinophils to lung in allergic bronchitis. In addition to IL-5, there are many factors affecting function of eosinophils.

Eosinophils are divided into subgroups, normodense eosinophils and hypodense eosinophils. Eosinophils have been shown to be hypodense eosinophils upon activation [Immunology, 47, 531 (1982)]. Hypodense eosinophils are also referred to as activated eosinophils. It has been reported that a qualitative change occurs in addition to a quantitative change in eosinophils in the peripheral blood of an HES patients [Clin. Exp. Immunol., 24, 423 (1976)]. Activated eosinophils have been implicated in the severity of HES symptom [Am. J. Cardiol., 52, 321 (1983)]. Aside from HES patients, activated eosinophils have been also found in the peripheral blood, and in bronchoalveolar lavage fluid (BALF) of a patient with bronchial asthma [Am. Rev. Respir. Dis, 132, 981 (1985)]. Various receptors, such as those of cytokines, are expressed on activated eosinophils (hypodense eosinophils) [J. Immunol., 142, 4416 (1989)]. Compared to normodense eosinophils, these hypodense eosinophils show elevated sensitivities against IL-5 [Clin. Exp. Immunol., 85, 312 (1991); J. Exp. Med., 172, 1347 (1990)].

The above-mentioned activated eosinophils are also known to survive in vitro without the cytokines inducing in the differentiation and proliferation of eosinophils [J. Exp. Med., 170, 343(1989)]. Thus, the properties of activated eosinophils are similar to those of eosinophils which infiltrate tissues, such as alveoli [Int. Arch. Allergy Immunol., 120, 91 (1999)]. A detailed explanation of why activated eosinophils become cytokine-independent remains unknown, however, their degranulation and prolonged survival are likely to be induced by various vital functional molecules other than IL-5.

Substances having inhibition activity on cytokines or chemokines that are involved in the differentiation or proliferation of eosinophils have been considered as agents that inhibit the eosinophil functions. However, in most cases these agents do not act on cytokine-independent eosinophils that have been activated and infiltrated into inflamed areas. Hence, eosinophil-specific inhibition and the induction of cellular death of activated eosinophils are necessary to inhibit the functions of any eosinophil.

However, no anti-inflammatory agent, so far, has been known to induce apoptosis of activated eosinophils.

Current major treatment for patients with eosinophilic diseases consists of administration with steroid. However, steroid administration is often associated with side effects. Specifically, the treatment has some other problems, such that patient's pathological condition may return to the original state when steroid administration is discontinued, and prolonged steroid administration may induce steroid resistance. As for now, it is difficult to inhibit the eosinophilia and there exists no way other than the symptomatic treatment thereof.

SUMMARY OF THE INVENTION

The development of a clinically more effective treatment having lower side effects has been long awaited for the treatment of inflammatory diseases, such as chronic bronchial asthma, and eosinophil associated diseases, such as eosinophilic granuloma.

Inventors of the present invention have found that human eosinophil-specific apoptosis induced by an anti-IL-5 receptor α-chain antibody with an Fc region of the human IgG1 subclass as disclosed in WO97/10354 is mediated by antibody-dependent cellular cytotoxicity. Since apoptosis of eosinophils mediated by antibody-dependent cellular cytotoxicity does not cause the release of cytotoxic proteins, reduced side effects can be expected. In addition, the inventors of the present invention have shown that the antibody induces apoptosis of IL-5-independent activated eosinophils, suggesting that the antibody is useful in the treatment for eosinophilic diseases.

Specifically, the present invention relates to the following (1) to (20):

(1) An apoptosis inducer, comprising an antibody which reacts specifically with an eosinophil and induces apoptosis of the eosinophil as an active ingredient.

(2) The apoptosis inducer of above mentioned (1), wherein the apoptosis-inducing antibody has antibody-dependent cellular cytotoxicity.

(3) The apoptosis inducer of above mentioned (1) or (2), wherein the antibody which reacts specifically with an eosinophil is an anti-human interleukin-5 receptor α-chain monoclonal antibody.

(4) The apoptosis inducer of above mentioned (3), wherein the anti-human interleukin-5 receptor α-chain monoclonal antibody is produced by an animal cell.

(5) The apoptosis inducer of above mentioned (3), wherein the anti-human interleukin-5 receptor α-chain monoclonal antibody is produced by a transformant KM8399 (FERM BP-5648).

(6) A therapeutic agent for eosinophilic diseases, comprising an antibody which reacts specifically with an eosinophil and induces apoptosis of the eosinophil as an active ingredient.

(7) The therapeutic agent for eosinophilic diseases of above mentioned (6), wherein the apoptosis-inducing antibody has cellular cytotoxicity.

(8) The therapeutic agent for eosinophilic diseases of above mentioned (6) or (7), wherein the antibody which reacts specifically with an eosinophil is an anti-human interleukin-5 receptor α-chain monoclonal antibody.

(9) The therapeutic agent for eosinophilic diseases of above mentioned (8), wherein the anti-human interleukin-5 receptor α-chain monoclonal antibody is produced by an animal cell.

(10) The therapeutic agent for eosinophilic diseases of above mentioned (8), wherein the anti-human interleukin-5 receptor α-chain monoclonal antibody is produced by the transformant KM8399 (FERM BP-5648).

(11) A method for specifically inducing apoptosis of an eosinophil using an antibody which reacts specifically with an eosinophil and induces apoptosis of the eosinophil.

(12) The method of above mentioned (11), wherein the apoptosis-inducing antibody has cellular cytotoxicity.

(13) The method of above mentioned (11) or (12), wherein the antibody which reacts specifically with an eosinophil is an anti-human interleukin-5 receptor α-chain monoclonal antibody.

(14) The method of above mentioned (13), wherein the anti-human interleukin-5 receptor α-chain monoclonal antibody is produced by an animal cell.

(15) The method of above mentioned (13), wherein the anti-human interleukin-5 receptor α-chain monoclonal antibody is produced by the transformant KM8399 (FERM BP-5648).

(16) A method for specifically reducing or removing eosinophils in peripheral blood or in a tissue infiltrated with eosinophils using an antibody which specifically reacts to an eosinophil and induces apoptosis of the eosinophil.

(17) The method of above mentioned (16), wherein the apoptosis-inducing antibody has antibody-dependent cellular cytotoxicity.

(18) The method of above mentioned (16) or (17) for specifically reducing or removing eosinophils, wherein the antibody which reacts specifically with an eosinophil is an anti-human interleukin-5 receptor α-chain monoclonal antibody.

(19) The method of above mentioned (18), wherein the anti-human interleukin-5 receptor α-chain monoclonal antibody is produced by an animal cell.

(20) The method of above mentioned (18), wherein the anti-human interleukin-5 receptor α-chain monoclonal antibody is produced by the transformant KM8399 (FERM BP-5648).

As the antibody used for the present invention, any antibody which reacts specifically to an eosinophil and induce apoptosis of the eosinophil can be used.

Examples of antibodies which react specifically to eosinophils include antibodies against receptors expressed on the surfaces of eosinophils. Examples of antibodies against receptors expressed on the surfaces of eosinophils include anti-human interleukin-5 receptor β-chain antibodies, anti-human interleukin-3 receptor antibodies, anti-human monocyte/macrophage colony-stimulating factor receptor antibodies, and anti-human interleukin-5 receptor α-chain (hereinafter, referred to as hIL-5R α) antibodies. The anti-hIL-5R α antibody is preferred.

Examples of antibodies which induce apoptosis of eosinophils include antibodies having activity to inhibit signal transduction involved in the differentiation or proliferation of eosinophils, and antibodies having cellular cytotoxicity. Antibodies having cellular cytotoxicity are preferred, in order to induce apoptosis of any eosinophil as described below.

Hence, examples of antibodies capable of reacting specifically with eosinophils and inducing apoptosis of the eosinophils include antibodies against receptors expressed on the surfaces of eosinophils, which have antibody-dependent cellular cytotoxicity, and preferably, anti-hIL-5R α antibodies which have antibody-dependent cellular cytotoxicity. Other examples of such antibodies include antibodies against receptors expressed on the surfaces of eosinophils, which are produced by animal cell lines, such as CHO cells, YB2/3.0-Ag20 cells, SP2/0-AG14 cells and NS0 cells, and preferably, anti-hIL-5R α antibodies which are also produced by animal cell lines. Further examples of such antibodies include human IgG1 type antibodies against receptors expressed on the surfaces of eosinophils, and preferably, human IgG1 type anti-hIL-5R α antibodies. An example is an anti-hIL-5R α human CDR-grafted antibody KM8399 produced by a transformant KM8399 (FERM BP-5648).

The anti-IL-5 receptor α-chain antibody can be produced by a method described in WO97/10354.

Apoptosis of eosinophils induced by the above antibody can be confirmed by the following method.

1. Isolation of Eosinophil (1) Isolation of Granulocyte from Peripheral Blood

Peripheral blood should be first treated with an anticoagulant to isolate the granulocytes from peripheral blood. Examples of anticoagulants include heparin sodium, disodium EDTA and dipotassium EDTA. Normally, 100 units of heparin sodium is used for 20 to 30 ml of peripheral blood.

Peripheral blood is collected with a syringe containing an anticoagulant, superposed on a suitable isolation medium, and centrifuged, thereby separating leukocytes into different cell populations, such as mononuclear cells, granulocytes and monocytes [Nature, 204, 793 (1964)].

Examples of media for separating peripheral blood-derived mononuclear cells (hereinafter referred to as PBMC) from granulocytes include Lymphoprep, Polymorphoprep (NYCOMED), Ficoll (Sigma) or the like. Further, isolation can also be performed using isotonic Percoll (Pharmacia) (0.15 M NaCl) adjusted to density of 1.085 to 1.088 by a densimeter. Centrifugation using the above isolation medium is always performed at room temperature.

(2) Isolation of Eosinophils From Granulocytes

Granulocytes separated in above mentioned (1) contain neutrophils and eosinophils, or may also contain erythrocytes. Erythrocytes can be removed through hemolyzation by either one of the following methods:

The pellet of granulocytes containing erythrocytes in a centrifuge tube is suspended in ice-cooled distilled water. After 30 seconds, an ice-cooled 1/10 volume of isosmotic 10-fold concentration buffer is added to stop hemolytic reaction. Centrifugation is carried out at 4° C. for 5 minutes at 400×g to remove the supernatant. Erythrocytes can be removed by repeating the procedure a few times.

Alternatively, the pellet of granulocytes containing erythrocytes is suspended in an ice-cooled 0.2% NaCl solution. After 15 seconds, an equivalent volume of ice-cooled 1.6% NaCl solution is added to stop the hemolytic reaction, followed by centrifugation at 4° C. for 5 minutes at 300×g, so that erythrocytes can also be removed [Clinical Immunology, 29., (Suppl. 17), 41 1997].

Subsequent to removal of erythrocytes, neutrophils should be removed.

Neutrophils expressing CD16 antigen on their surface can be removed by performing sorting.

First, granulocytes are incubated with mouse anti-CD 16 antibodies and then sheep anti-mouse immunoglobulin antibody immobilized on the Dynabead™ (DYNAL) is added. Using Magnetic bead concentrator MPC-1 (DYNAL), Dynabead-bound CD 16 positive cells are captured to collect the remaining suspended cells, thereby isolating the eosinophils (Allergy, 50, 34 (1995); Eur. J. Immunol., 24, 518 (1994); J. Immunol. Methods, 122, 97 (1989)).

Neutrophils can also be separated from granulocytes by MACS™ system (Miltenyi) using anti-CD 16 antibody immobilization microbeads (J. Immunol. Methods, 165, 253 (1993), J. Immunol. Methods 127, 153 (1990)).

(3) Induction of Activated Eosinophil

Activated eosinophils can be obtained by culturing for a few days of above-mentioned (2) with IL-3[J. Clin. Invest., 81 1986 (1988)], or by co-culturing with PBMC for 2 days. Furthermore, blood collected from a body is centrifuged with cell isolation media of different densities, so that activated eosinophils which have densities lower than the normal levels can be obtained [Clin. Exp. Immunol., 85, 312 (1991)].

The presence of activated eosinophils can be confirmed by the expression of CD69 molecules [J. Exp. Med., 172, 701 (1990)].

(4) Method for Culturing Eosinophils

Eosinophils can be cultured in RPMI1640 media supplemented with 1% or 10% fetal calf serum (hereinafter referred to as FCS), to which any one of cytokines including IL-5, IL-3 and GM-CSF is added at a final concentration of 1 ng/ml under the air containing 5% $CO_2$ at 37° C.

2. Method for Inducing Apoptosis of Human Eosinophils by Antibodies

Inhibition of signal-transduction involved in the differentiation and proliferation of eosinophils causes normodense eosinophils to die. However, the inhibition of signal-transduction involved in differentiation and proliferation of eosinophils is not enough to cause hypodense eosinophils (activated eosinophils) to die. Hypodense eosinophils cause effector function of antibody such as complement-dependent cytotoxicity (CDC), antibody-dependent cellular cytotoxicity (ADCC) or the like to die.

There are two types of cell death, necrosis and apoptosis. However, the mechanism of action is yet to be elucidated.

Apoptosis can be induced by cytotoxic activity of antibody [Cancer Imunol. Immunother, 43, 220 (1996)]. However, the cellular cytotoxicity causes not only apoptosis, but also necrosis.

Cell death of eosinophils induced by treating antibody used for the present invention having cellular cytotoxicity can be analyzed by the following.

An example of a method for detecting necrotic cells involves staining intracellular DNA with PI (Propidium Iodide) reagent; and an example of a method for detecting apoptotic cells uses annexin V. Specifically, apoptotic cells can be evaluated by measuring cell surface phosphatidylserine (hereinafter referred to as PS) with annexin V [J. Immunol. Methods, 217, 61 (1998)] as an indication as described in the following method.

PS on the cell membrane is located on the side of cytoplasm in a living cell. When apoptosis is induced, PS is exposed on the cell surface within 1 hour. Accordingly, FITC-labeled annexin V which binds to PS in a calcium-dependent manner can detect the PS exposed apoptotic cells, so that early apoptosis can be detected before the cell membrane is damaged [J. Exp. Med. 182, 1545 (1995)].

Double staining with annexin V-FITC and PI is preferred, because binding of annexin V to cell membranes may also be observed in necrotic cells. Early apoptosis can be detected by the fact that it is stained with annexin V-FITC, but not with PI.

The antibody-dependent cellular cytotoxicity (hereinafter abbreviated as ADCC) can be measured according to the method of 3 described later. Thus induction of apoptosis in the target cells can be evaluated using the annexin V method.

3. Measurement of ADCC Activity

To measure ADCC activity, effector cells and target cells are used.

Examples of effector cells include natural killer (NK) cells, large granular lymphocytes (LGL), and PBMC comprising NK and LGL, or leukocytes having Fc receptors on the cell surfaces, such as neutrophils, eosinophils and macrophages.

Effector cells can be isolated according to the method of above mentioned 1.

As the target cells, any cells which express, on the cell surfaces, antigens that antibodies to be evaluated can recognize can be used. An example of such a target cell is an eosinophil which expresses IL-5 receptor on the cell surface.

Target cells are labeled with a reagent that enables detection of cytolysis.

Examples of reagents for labeling include a radio-active substance such as sodium chromate ($Na_2{}^{51}CrO_4$, hereinafter referred to as $^{51}Cr$) [Immunology, 14, 181 (1968)], calcein-AM [J. Immunol. Methods, 172, 227 (1994)], Europium [J. Immunol. Methods, 184, 29 (1995)] and $^{51}Cr$ is preferred.

When human peripheral blood eosinophils, which are terminally differentiated cells and have low labeling efficiency, are used as target cells, the death of target cells should be detected by another method after ADCC reaction. In this situation, cell death can be detected by the method described in above mentioned 2.

4. Method for Specifically Reducing or Removing Eosinophils in Peripheral Blood or in Tissues Infiltrated With Eosinophils Eosinophils can be specifically reduced or removed from peripheral blood or tissues infiltrated with eosinophils using an apoptosis inducer which comprises, as an active ingredient, an antibody of the present invention that specifically reacts to the eosinophils and induces apoptosis of the eosinophils. Examples of such antibodies as an active ingredient include anti-hIL-5R α-chain antibodies, or preferably anti-hIL-5R α antibodies produced by animal cells. For example, direct action of anti-hIL-5R α-chain monoclonal antibodies KM8399 on peripheral blood or tissues enables induction of eosinophil apoptosis, and reduction or removal of eosinophils in peripheral blood or tissues infiltrated with eosinophils.

5. Form of Agent

The above-described apoptosis inducer or the therapeutic agent for eosinophilic diseases comprising, as an active ingredient, an antibody which specifically reacts to eosinophils and induces apoptosis of the eosinophils, may be solely administered as an agent. Normally, the inducer or the therapeutic agent is preferably provided as pharmaceutical preparations which are produced by mixing with one or more pharmacologically acceptable carriers according to any method known in the pharmaceutical technical field.

It is preferable to use an administration which is most effective in carrying out a treatment. Examples include oral administration and parenteral administration such as intraoral, bronchial, intrarectal, subcutaneous, intramuscular, intravenous administrations and the like. In an antibody-containing pharmaceutical formulation, intravenous administration is preferrable.

Examples of dosage form include nebulae, capsules, tablets, granules, syrups, emulsions, suppositories, injection, an ointments, tapes and the like.

Examples of formulation suitable for oral administration include emulsions, syrups, capsules, tablets, powders, granules and the like.

Liquid preparations, such as emulsions and syrups, can be produced by using as an additive, water; sugar, such as sucrose, sorbitol, fructose etc.; glycol, such as polyethylene glycol, propylene glycol etc.; oil, such as sesami oil, olive oil, soybean oil etc.; antiseptic such as p-hydroxy benzoate ester etc.; flavoring, such as strawberry flavors, peppermint flavors; and the like.

Capsules, tablets, powders, granules or the like can be produced by using as an additive, excipients such as lactose, glucose, sucrose, mannitol etc.; disintegrators, such as starch, sodium alginate etc.; lubricants, such as magnesium stearate, talc etc.; binders, such as polyvinyl alcohol, hydroxypropylcellulose, gelatin etc.; surfactants, such as fatty acid ester etc.; plasticizers, such as glycerine etc; and the like.

Examples of pharmaceutical preparations suitable for parenteral administration include injectables, suppositories, nebulae and the like.

An injection is prepared by using a carrier or the like which comprises a saline solution, a glucose solution, a mixture of both or the like.

A suppository is prepared by using a carrier, such as cacao butter, hydrogenated fat, carboxylic acid and the like.

A nebula is prepared by using the antibody preparation itself or using a carrier or the like which facilitates absorption by allowing the compound to disperse as fine particles without stimulating the mouth cavity and bronchial mucous membrane of a recipient.

Examples of carriers include lactose, glycerine and the like. Preparations, such as aerosol and dry powder, can be used, depending on the properties of the antibody and the carrier to be used. In addition, these parenteral preparations can be supplemented with components illustrated as additives for oral preparations.

The applied dose and the number of administration vary depending on target therapeutic effects, medication methods, treatment period, age and body weight of the patient. Normally, 10 μg/kg to 8 mg/kg is administered per day to an adult patient.

The term "eosinophil associated diseases" of the present invention refers to diseases caused by eosinophils, including allergic diseases, such as asthma bronchiale and atopic dermatitis; and hypereosinophilic syndrome (HES), such as eosinophilia (e.g., eosinophilic pneumonia and sudden eosinophilia), eosinophilic enterogastritis, eosinophilic leukemia, eosinophilic granuloma and Kimura's disease.

The apoptosis inducer and the therapeutic agent for eosinophilic diseases of the present invention can be used as the therapeutic agent for the above eosinophil associated diseases.

BEST MODE FOR CARRYING OUT THE INVENTION

EXAMPLE 1

Isolation of Human PBMC and Eosinophils

Figure 1:
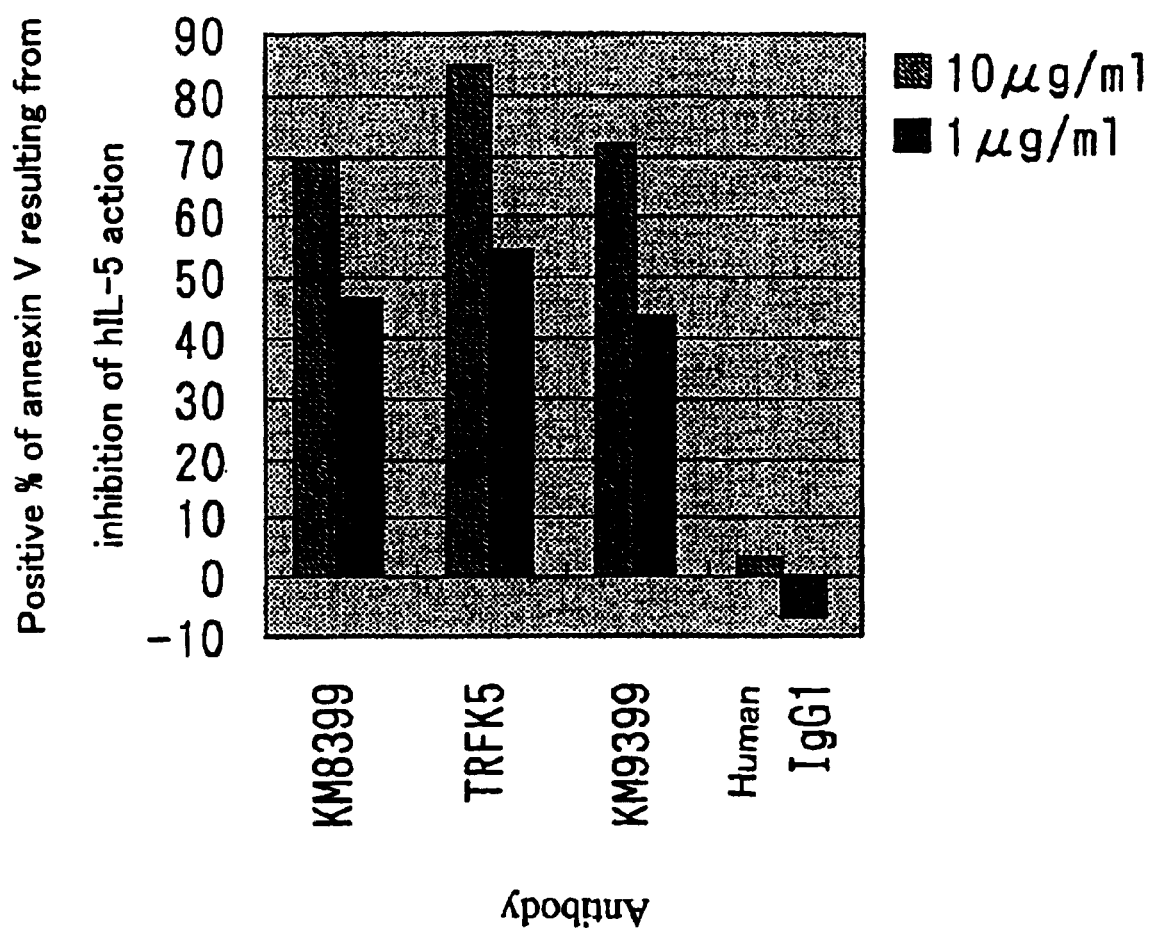
FIG. 1 shows the in vitro inhibitory effect on the IL-5-dependent survival of eosinophils isolated from peripheral blood. The vertical axis indicates the positive % of annexin V resulting from the inhibition of recombinant human IL-5 action (hereinafter referred to as rhIL-5), and the horizontal axis indicates each antibody. Human IgG1 was used as a negative control.

Sixty ml of normal human peripheral blood was collected using a syringe containing 200U (200 µl) of a solution of heparin sodium for injection (Takeda Chemical Industries, Ltd.). The total volume was diluted twice with the equivalent volume of saline (Otsuka Pharmaceutical Co., Ltd.) to obtain a final volume of 120 ml. Five ml of Lympho-prep (NY-COMED) was apportioned to twelve 15 ml centrifuge tubes (SUMITOMO BAKELITE Co., Ltd.), and then 10 ml of the diluted peripheral blood was superposed over each Lympho-prep, followed by centrifugation at 800×g for 20 minutes at room temperature. A PBMC fraction between the plasma layer and the Lympho-prep layer was collected from all the centrifuge tubes, suspended in RPMI1640 media containing 1% FCS (GIBCO, hereinafter referred to as 1% FCS-RPMI), and then washed twice by centrifugation at 400×g for 5 minutes at 4° C., thereby preparing effector cells. The portions other than the precipitation layers containing erythrocytes were removed with an aspirator from the 15 ml centrifuge tubes. The precipitation layers remaining in the four tubes were collected into one 50 ml centrifuge tube (FALCON) with a transfer pipette. Next, the precipitation layers were suspended in 27 ml of ice-cooled distilled water, so as to hemolyze the blood erythrocytes. Thirty seconds later, 3 ml of a PIPES buffer at a 10-fold concentration, comprising 0.11M sodium chloride, 5 mM potassium chloride, 25 mM piperazine-1,4-bis (2-ethanesulfonic acid) and 42 mM sodium hydroxide, was added to the tube, so as to reestablish isotonicity and stop the reaction. Then, centrifugation at 400×g for 5 minutes at 4° C. was carried out. The supernatant was decanted, and then the precipitate was well suspended in 3 ml of a PIPES buffer. Then the similar procedure was repeated and the precipitates in all the centrifuge tubes were transferred into one 15 ml centrifuge tube, and then the precipitate was washed with 15 ml of a PIPES buffer containing 1% FCS (hereinafter referred to as 1% FCS-PIPES). The cell population was prepared as a granulocyte fraction (approximately $4 \times 10^7$ to $6 \times 10^7$ cells) and the number of cells was counted. Subsequently, 2 µg of mouse anti-CD16 antibodies (Clone name: 3G8, IMMUNOTECH) was added to $1 \times 10^7$ cells. The antibodies and the cells were allowed to react in ice with occasional stirring for 30 minutes. The mixture was washed twice by centrifugation with 1% FCS-PIPES, and then sheep anti-mouse antibody-immobilized magnetic beads (DYNAL) in a 4-fold volume of the number of cells were added to the mixture, followed by reaction in ice for 30 minutes with occasional stirring. Using a magnetic bead concentrator MPC-1 [DYNAL], the magnetic beads and CD16-expressing cell populations bound to the beads were removed. Only the remaining supernatant was transferred into a 15 ml centrifuge tube, centrifuged at 400×g for 5 minutes at 4° C., thereby collecting the cells. The number of cells in the pellet was counted, and the cell population was used as an eosinophil fraction (approximately $1 \times 10^6$ to $2 \times 10^6$ cells). The cells were prepared into specimens with a Cytospin (SHANDON), and then the specimens were stained with a Dif-Quick stain (INTERNATIONAL REAGENTS CORPORATION). Approximately 500 cells were counted using a microscope so that the purity of eosinophils was calculated. Eosinophils could be always isolated with a purity of 95% or more.

EXAMPLE 2

Detection of Apoptosis of Eosinophils Based on Inhibition of IL-5 Activity

The inhibition of survival of eosinophils was measured in vitro for each antibody by measuring annexin V-positive apoptotic cells as shown below. The antibodies used herein were KM8399 and KM9399 (WO97/10354), which are anti-human IL-5R α-chain antibodies; TRFK5 (Pharmingen), which is an anti-human IL-5 antibody; and KM8969, which is a human IgG1, anti-ganglioside GM2 monoclonal antibody as a control antibody (Japanese Patent Application Laying-Open (Kokai) No. 10-257893).

High purity (purity of 95% or more) eosinophils isolated by the method of Example 1 were prepared at $2 \times 10^6$ cells/ml with 1% FCS-RPMI. Then, 100 µl of the prepared eosinophils was apportioned to each well of a 96-well U-shaped plate.

It is known that Eosinophils prolong their lifetime in the presence of 0.1 ng/ml rhIL-5 (R&D). Thus, 0.4 ng/ml rhIL-5 was apportioned at 50 µl/well.

Each type of antibody was prepared at 4 µg/ml was apportioned at 50 µl/well. In total, 200 µl of the prepared solution was cultured under the air containing 5% $CO_2$, at 37° C. for 24 hours.

After culturing, the eosinophils in the wells were stained using an annexin V-FITC kit (TREVIGEN). Forward-scattered light (hereinafter referred to as FS) and side-scattered light (hereinafter referred to as SS) were set on the fractions of the cells that have kept their cell forms. Then FL1 (the first fluorescence) was measured by a flow cytometer (Coulter), so as to calculate the proportion of annexin V-FITC positive cell population to the total number of subject cells. Therefrom, the proportion of apoptosis-induced cells was obtained. Specifically, the proportion of apoptosis-induced cells was calculated by taking rhIL-5-free annexin V-FITC positive % in the absence of rhIL-5 as 100%, annexin V-FITC positive % in the presence of rhIL-5 and in the absence of antibody as 0%.

As shown in FIG. 1, KM8399 and TRFK5 induced the apoptosis of eosinophils based on inhibition of rhIL-5 activity to almost the same degree. KM9399 (WO97/10354), which is a human IgG4 subclass having no cellular cytotoxicity, also has the similar activity. These results suggest that the apoptosis of eosinophils was induced by inhibiting IL-5 activity.

EXAMPLE 3

Detection of Apoptosis of Eosinophils Induced by Cellular Cytotoxicity (1) Detection of Apoptosis Induced by ADCC Using Effector Cells (I)

A 96-well U-shaped plate (FALCON) for cell cultivation was used. PBMC fractions from healthy volunteers, as prepared in above mentioned Example 1, were used as effector cells, and prepared at $1 \times 10^7$ cells/ml with 1% FCS—RPMI. The cell suspension was apportioned at 100 µl/well. As target cells, the fractions of eosinophils as prepared in Example 1 were prepared at $8 \times 10^5$ cells/ml, and then apportioned at 50 µl/well. At this time, the effector/target ratio (E/T ratio) was approximated to be 25:1, which is similar to the ratio in vivo.

Next, 4 µg/ml KM8399 antibody diluent was added at 50 µl/well, and then the plate was allowed to stand under the air containing 5% $CO_2$ at 37° C. for 4 hours for ADCC reaction to proceed.

After reaction, media were removed from the wells, and then the cells were stained using an annexin V-FITC kit (TRE-VIGEN) according to the instruction attached to the kit, followed by analysis with a flow cytometer. FS and SS were set on the subject cells (the fractions of the eosinophils) in the samples, and then the fluorescence intensity of FL1 was measured. Therefrom, the proportion of annexin V positive % to eosinophil fractions was calculated.

Figure 2:
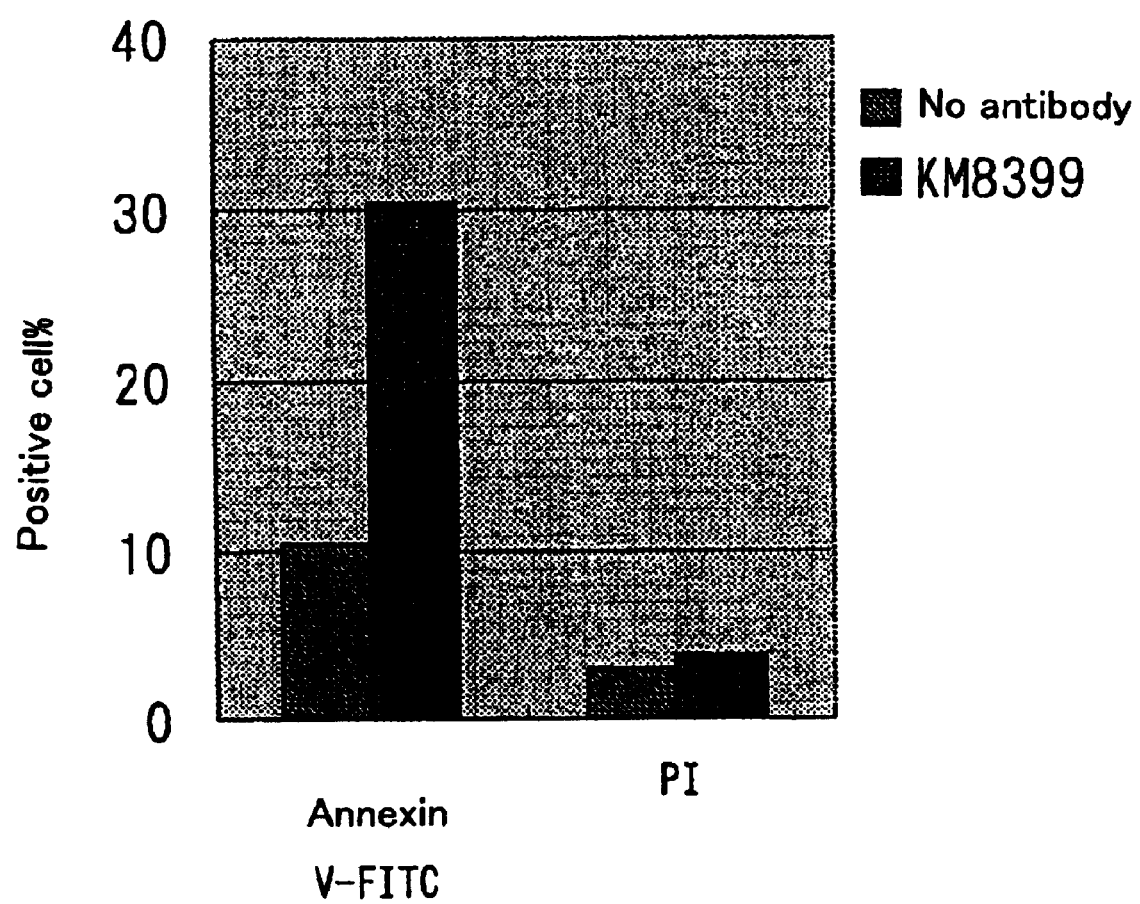
FIG. 2 shows the stainability of eosinophils fractions for each reagent after reaction with antibodies. The vertical axis indicates each reagent's positive % in the total number of eosinophils, and the horizontal axis indicates the staining reagents. "Annexin V-FITC positive cells" indicate apoptotic cells, and "PI positive cells" indicate necrotic cells.

As shown in FIG. 2, when KM8399 was added, the annexin V-FITC positive cell population significantly increased, compared to the samples to which antibody was not added, however, the PI positive cell population did not increase.

These results suggest that the mechanism of KM8399 to remove eosinophils is induction of apoptosis.

(2) Detection of Apoptosis Induced by ADCC Using Effector Cells (II)

Detection was carried out in a similar manner to Example 3 (1) except that the time of ADCC reaction was 20 hours. Apoptosis was examined by staining with annexin V only. To measure with a flow cytometer based on differences between FS and SS, areas to be measured with the fluorescence intensity of annexin V were determined respectively for lymphocytes, monocytes and eosinophils. The annexin V positive % of each subject area was detected by the method described in Example 3 (1).

Added as antibodies were KM8399, the IgG1 type antibody having ADCC activity; and KM9399, the IgG4 type antibody having almost no ADCC activity. Added as control antibodies were KM871, the IgG1 type antibody anti-ganglioside GD3 monoclonal antibody (Cancer Immunol. Immunother., 3, 373-380, 1993). These antibodies were all examined at a final concentration of 1 µg/ml.

Figure 3:
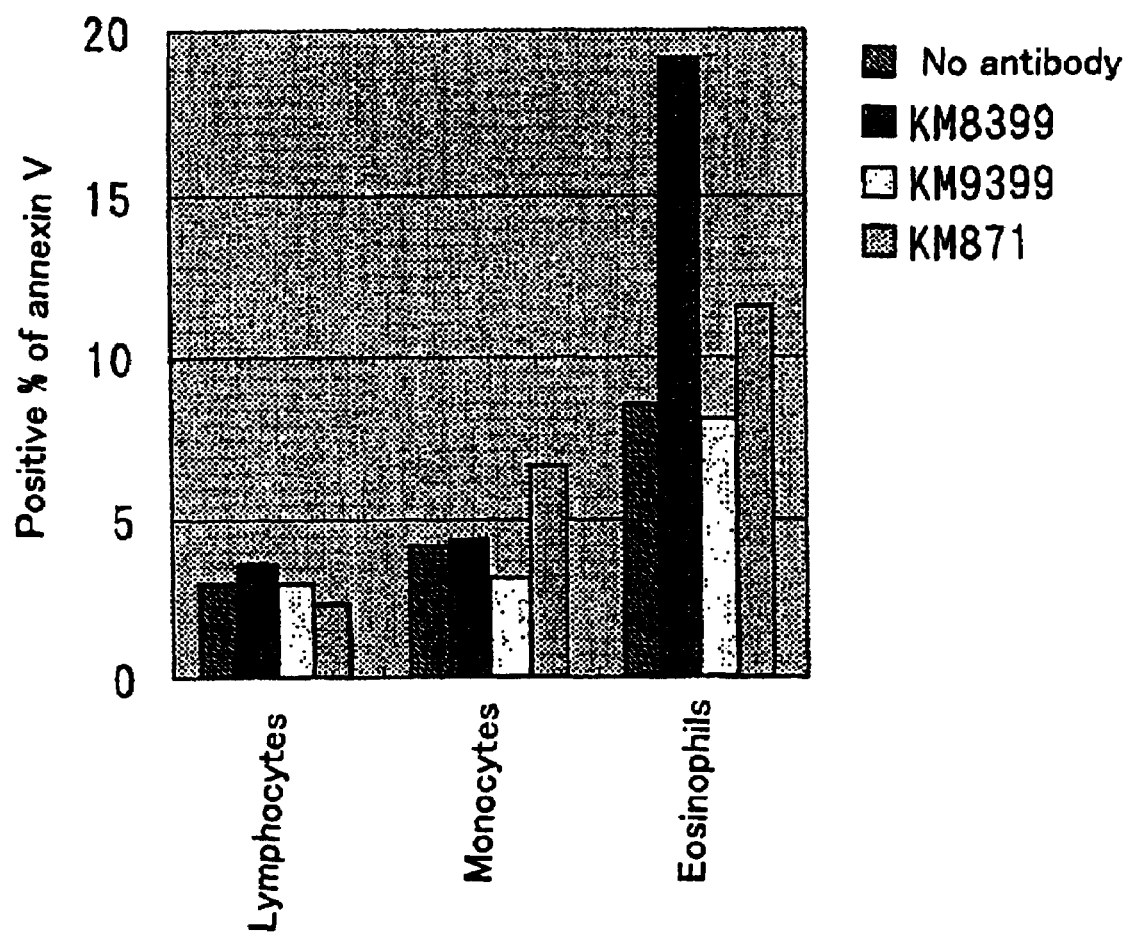
FIG. 3 shows the specificity for cell of the apoptosis-inducing activity of KM8399. The vertical axis indicates the positive % of annexin V, and the horizontal axis indicates each cell population.

As shown in FIG. 3, when KM8399, the IgG1 type antibody having ADCC activity, was added, eosinophil-specific induction of apoptosis was observed, however, no reaction was found in the lymphocytes fraction and monocytes fraction contained in the PBMC fraction. When KM9399, the IgG4 type antibody having no ADCC activity, was added, no reaction was observed in any of the cells. These results suggest an ADCC activity-related apoptosis induction mechanism by KM8399. KM871, the IgG1 type anti-ganglioside GD3 monoclonal antibody (Cancer Immunol. Immunother., 36, p373-380, 1993) as a negative control indicates no specific activity.

(3) Comparison with Anti-IL-5 Antibody TRFK5

To determine whether the detected level of eosinophil apoptosis induction by KM8399 as shown in Example (2) was significant, comparisons with TRFK5 were examined using the PBMC fractions of 3 healthy volunteers in a manner similar to the method of Example 3 (1).

Figure 4:
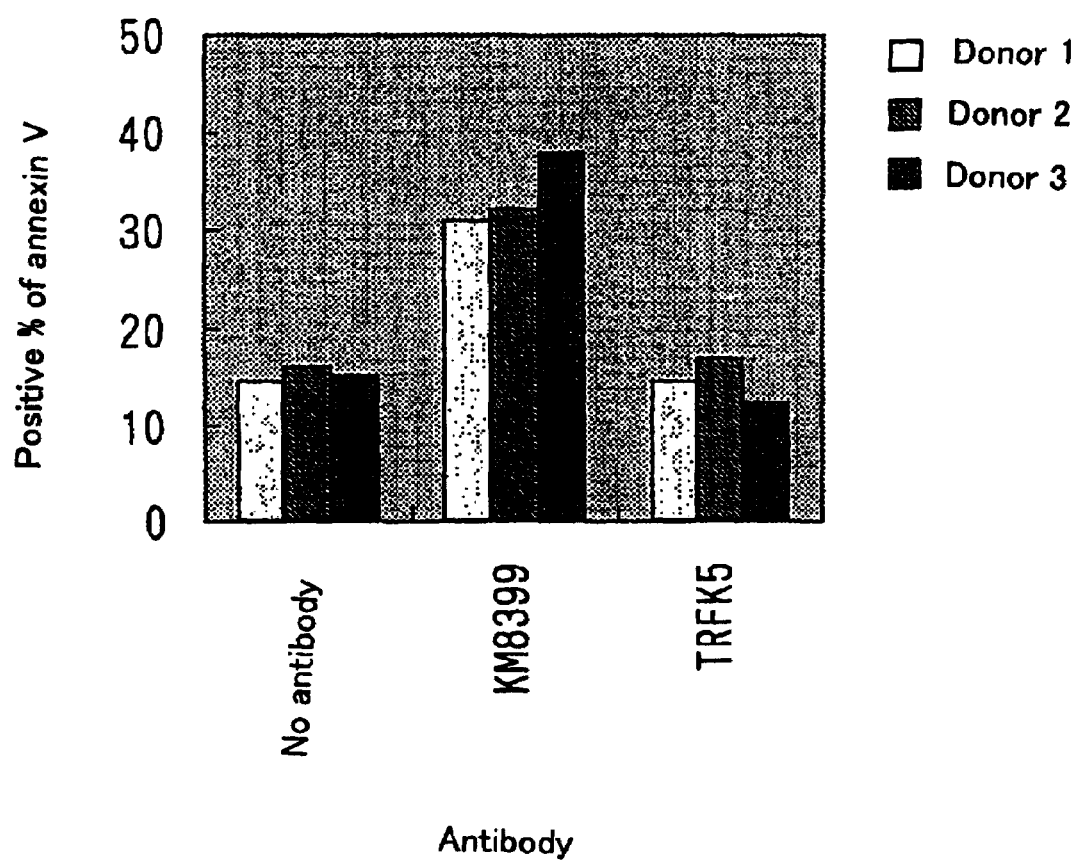
FIG. 4 shows the apoptosis-inducing activity of KM8399 and TRFK5. The vertical axis indicates the positive % of annexin V, and the horizontal axis indicates the antibodies added.

As shown in FIG. 4, although apoptosis induction was observed when KM8399 was added, no apoptosis induction was observed when TRFK5 was added.

A similar experiment carried out using the PBMC fractions of 3 healthy volunteers yielded similar results.

Figure 5:
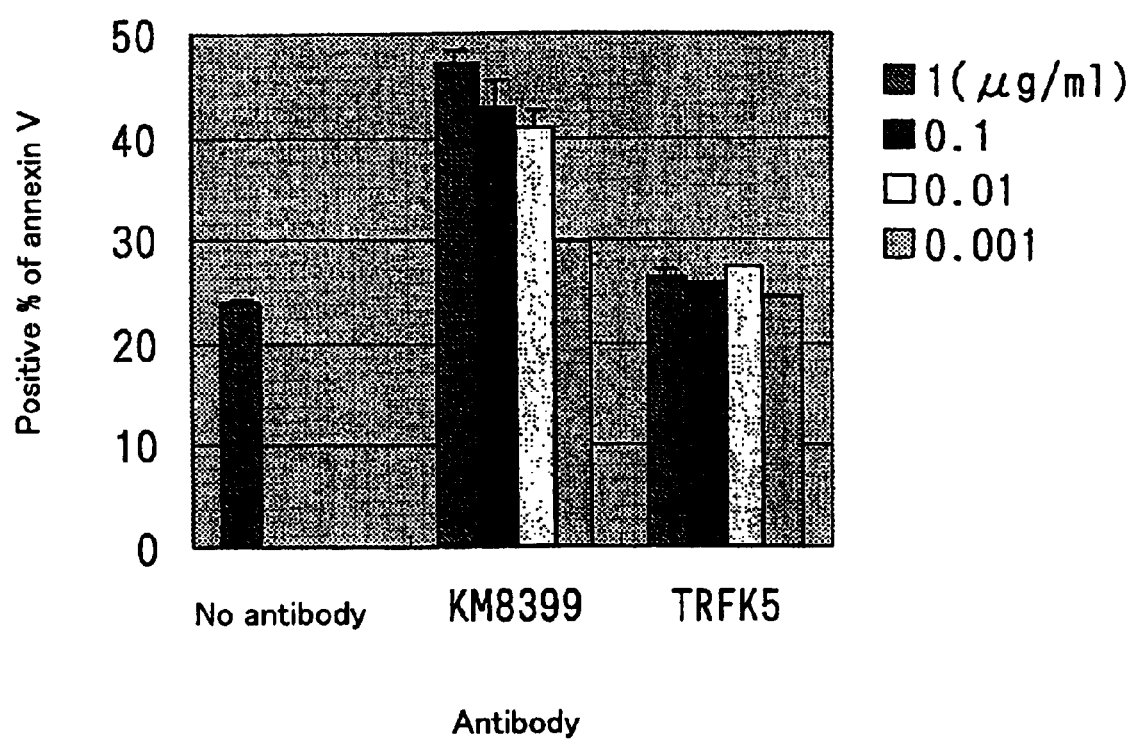
FIG. 5 shows the dose dependency of the apoptosis-inducing activity of KM8399. The vertical axis indicates the positive % of annexin V, and the horizontal axis indicates the antibodies added.

Further, an experiment was carried out in a manner similar to the above experiment using different concentrations of antibodies. The results are shown in FIG. 5. KM8399 showed an increase in apoptosis-inducing activity in an antibody concentration-dependent manner, and a sustained level of activity even at the final concentration of 0.01 µg/ml. These results suggest that KM8399, the anti-human IL-5 receptor α-chain antibody having eosinophil-specific binding activity, possesses higher apoptosis-inducing activity, and is more preferred as a therapeutic agent for eosinophilic diseases, compared to TRFK5, the anti-human IL-5 antibody.

(4) ADCC Activity in the Presence of Cytokines

ADCC activity was examined, when eosinophils were activated in the presence of IL-5, IL-3 and/or GM-CSF, and then various antibody types (1 µg/ml each) were acted upon the eosinophils.

PBMC fractions prepared at a 2-fold concentration of the PBMC fractions used in Example 3(1) were apportioned at 50 µl/well; a 4 ng/ml diluent of each cytokine or a 12 ng/ml mixed solution of 3 types of cytokines was apportioned at 50 µl/well; and then the fractions of eosinophils and antibody diluents were apportioned at 50 µl/well, similar to Example 3 (1), so as to achieve the total volume of 200 µl/well. The cytokines added herein was either IL-5, IL-3 and/or GM-CSF (all the cytolines manufactured by R&D). The mixed solution of the cytokines contained the above 3 types of cytokines (4 ng/ml).

Figure 6:
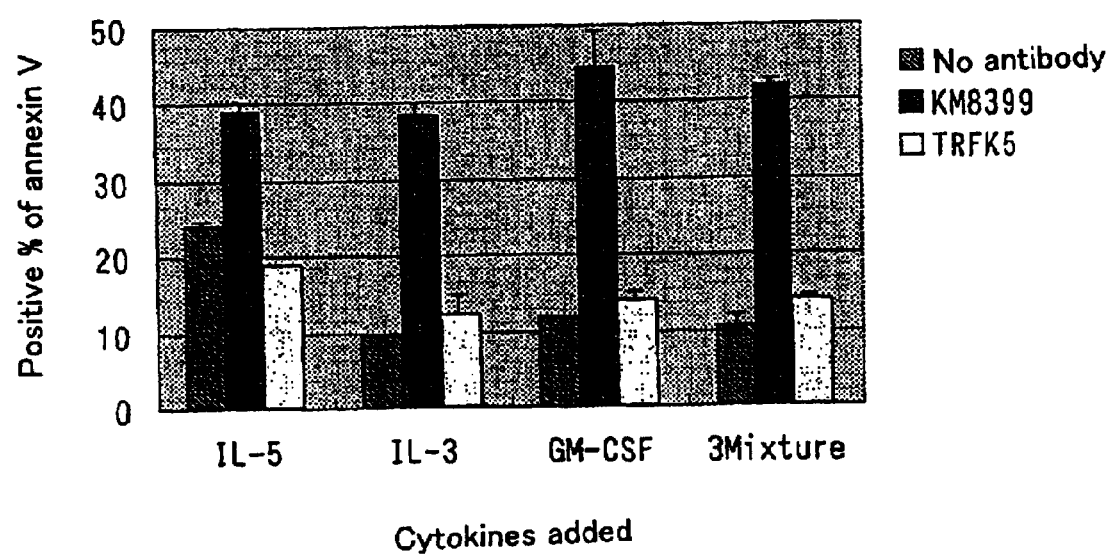
FIG. 6 shows apoptosis-inducing activity in the presence of various cytokines. The vertical axis indicates the positive % of annexin V, and the horizontal axis indicates the cytokines added.

As shown in FIG. 6, 1 µg/ml KM8399 significantly induced apoptosis compared to the case that no antibody is added in the presence of any one or all of the cytokines. In contrast, TRFK5 induced no apoptosis.

EXAMPLE 4

Measurement of Eosinophil Granular Protein

After ADCC reaction was carried out in a similar manner to Example 3 (1), the plate was subjected to centrifugation at 350×g for 5 minutes at 4° C., the supernatants were transferred into a 1.5 ml tube (Eppendorf), stored at 80° C., and then used as samples for quantitatively determining free eosinophil granular protein, as described below. To measure all the granular proteins in the cells, 1% FCS-RPMI containing 10% Triton X was added at 10 µl/well, cytolysis was performed, and then the culture supernatants were used as samples.

(1) Measurement of Eosinophil Peroxidase: EPO

Figure 7:
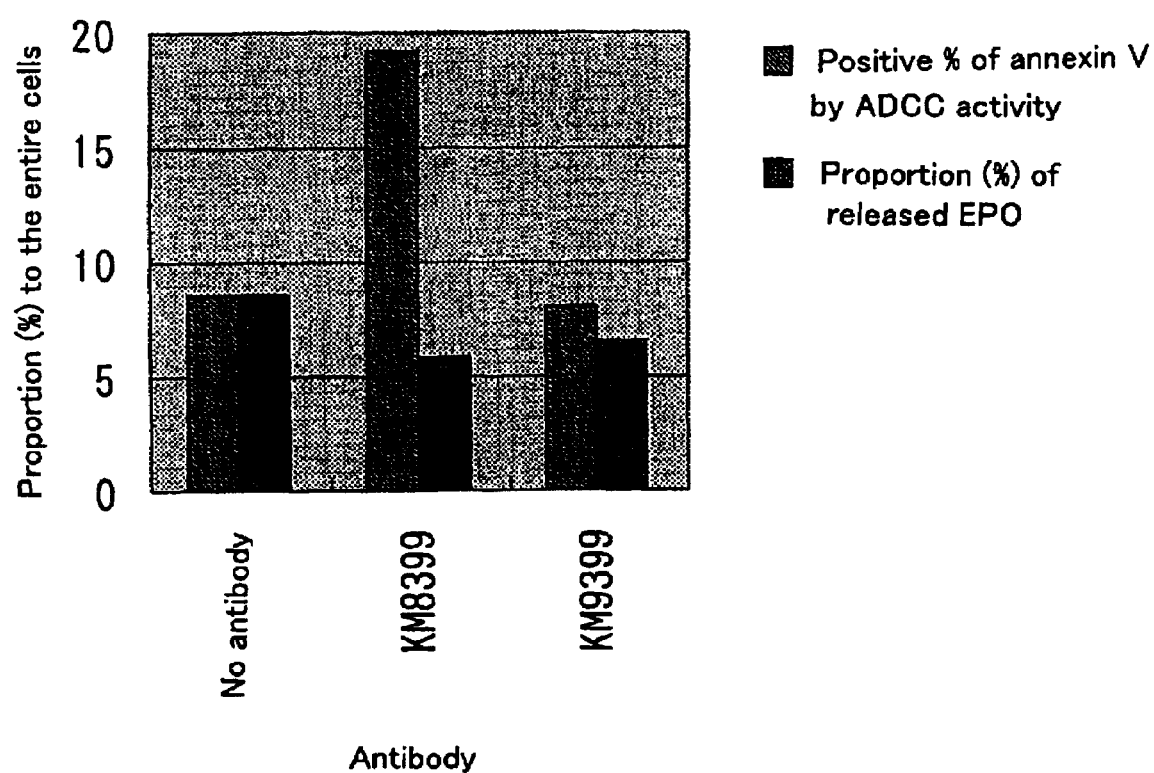
FIG. 7 shows the quantitatively determined values of eosinophilic granular protein (EPO) released after ADCC reaction. The vertical axis indicates the proportions (%) of released EPO to the total EPO, and the horizontal axis indicates the antibodies added.

50 µl of the culture supernatant sample was apportioned in duplicate to each well of a 96-well ELISA plate (Greiner), and then a chromogenic substrate solution [solution consisting of 50 mM sodium citrate (pH5.0), 0.4 mg/ml o-phenylene diamine and 30% hydrogen peroxide solution 1/1000] was added at 100 µl/well. The mixture was allowed to develop color for 30 minutes. Subsequently, 4N sulfuric acid was added at 50 µl/well to stop color development, and then the absorbance at 490 nm was measured using a plate reader (Molecular Devices). As shown in FIG. 7, the release % of EPO in the sample added with KM8399 was equivalent to that in the sample to which no antibody was added.

Figure 8:
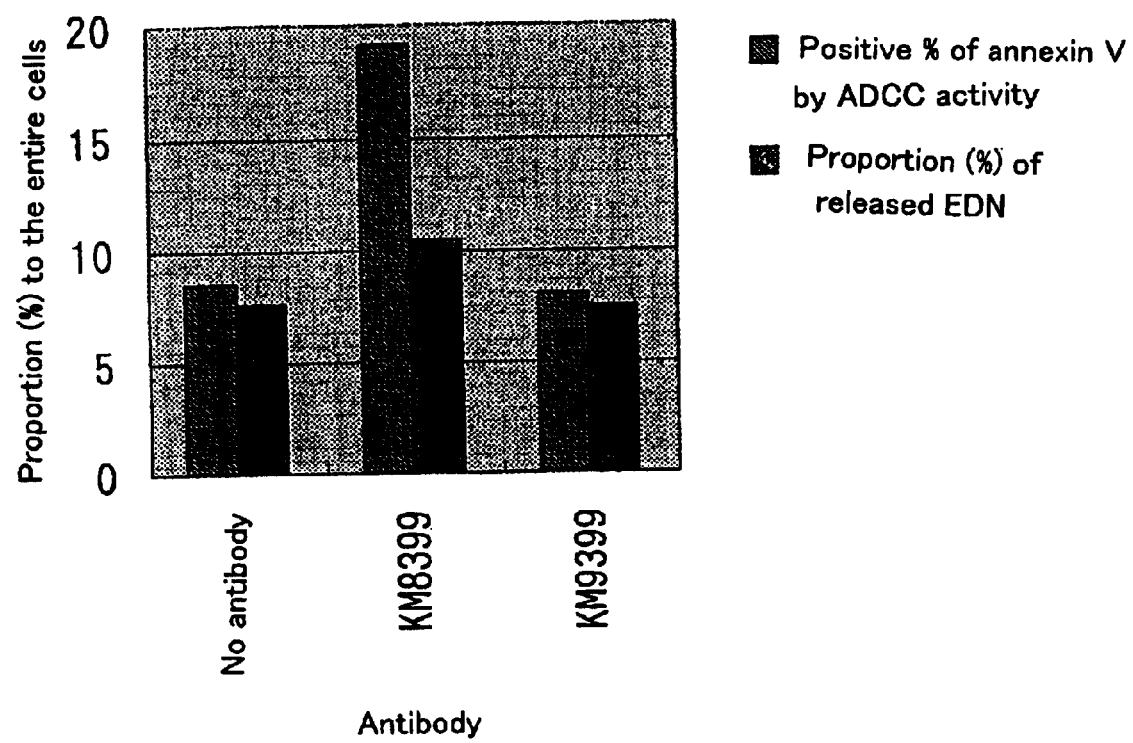
FIG. 8 shows the quantitatively determined values of eosinophilic granular protein (EDN) released after ADCC reaction. The vertical axis indicates the proportions (%) of released EDN to the total EDN, and the horizontal axis indicates the types of antibodies added.

(2) Measurement of Eosinophil-Derived Neurotoxin (EDN) 200 µl of an assay diluent contained in an EDN ELISA kit (MBL) was added to 50 µl of the culture supernatant following ADCC reaction, and then diluted 5-fold, thereby preparing samples for measurement. The samples were prepared in duplicate, and EDN was quantitatively determined according to the instructions of the kit. The absorbance was measured with a plate reader (Molecular Devices), and the concentrations in the samples were converted based on a standard product in the kit using soft max (Molecular Devices). As shown in FIG. 8, the release % of EDN in the sample added with KM8399 was significantly lower, and showed no significant difference compared to that in the sample to which no antibody was added.

As described above, it could be confirmed that removal of eosinophils by KM8399 was caused by apoptosis, and not by necrosis in which cytoplasms such as EPO and EDN are fragmented and scattered. Specifically, when eosinophils were removed by KM8399, no toxicity resulting from the release of granular proteins within the eosinophils was observed to affect the surrounding tissues or the cells.

EXAMPLE 5

Morphological Evaluation of Viability of Eosinophils After ADCC Reaction

Figure 9:
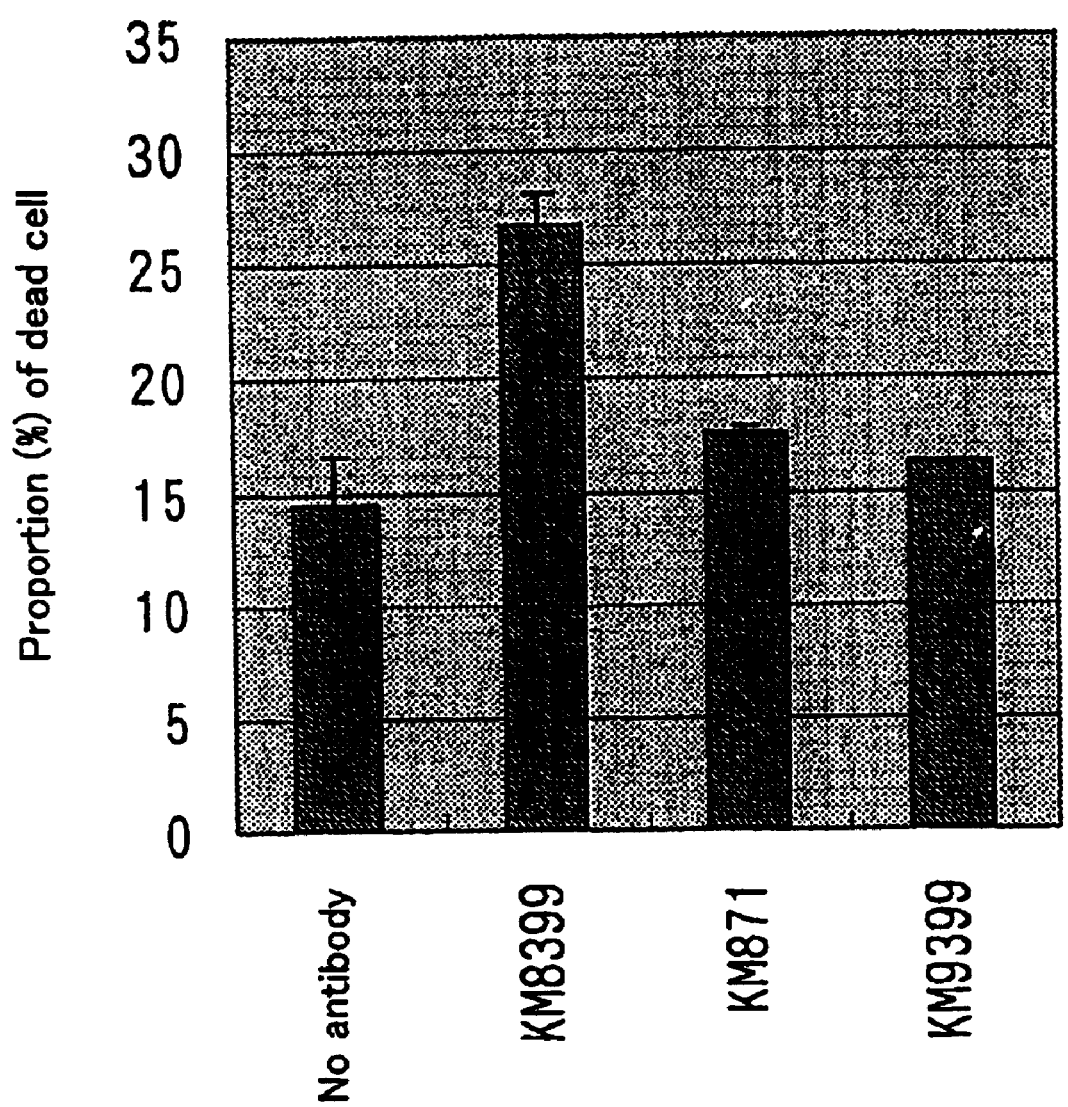
FIG. 9 shows the viability of eosinophils. The vertical axis indicates dead cells (%), and the horizontal axis indicates the antibodies added.

After ADCC reaction, 30 μl of a reaction solution containing the cells was diluted 10-fold with 1% FCS-RPMI. 100 μl of the diluted solution was applied to each sheet of slide glass (SHANDON), and two specimens were prepared with Cytospin for each sample. Similar to the evaluation of the purity of eosinophils, specimens were stained with Dif-Quick stain (INTERNATIONAL REAGENTS CORPORATION). Next, 100 cells comprising viable and dead eosinophils (cells that nearly kept their forms) on each slide glass were counted under a microscope, thereby calculating the proportion of dead cells. As shown in FIG. 9, eosinophil-specific removal resulting from the addition of KM8399 was confirmed, similar to the result of apoptosis induction obtained using annexin V. Neither IgG4 type KM9399 nor the negative control, IgG1 type anti-ganglioside GD3 monoclonal antibody KM871 [Cancer Immunol. Immunother., 36, p373-380, 1993], did not induce eosinophil-specific removal.

EXAMPLE 6

Concentration of CD16 Positive Cells in the Peripheral Blood Granulocyte

Granulocytes in peripheral blood consist of CD16 positive neutrophil and CD16 negative eosinophil fractions. Selective removal of eosinophils from peripheral blood granulocytes was studied by measuring the proportion of CD16 positive cells by the following method.

Figure 10:
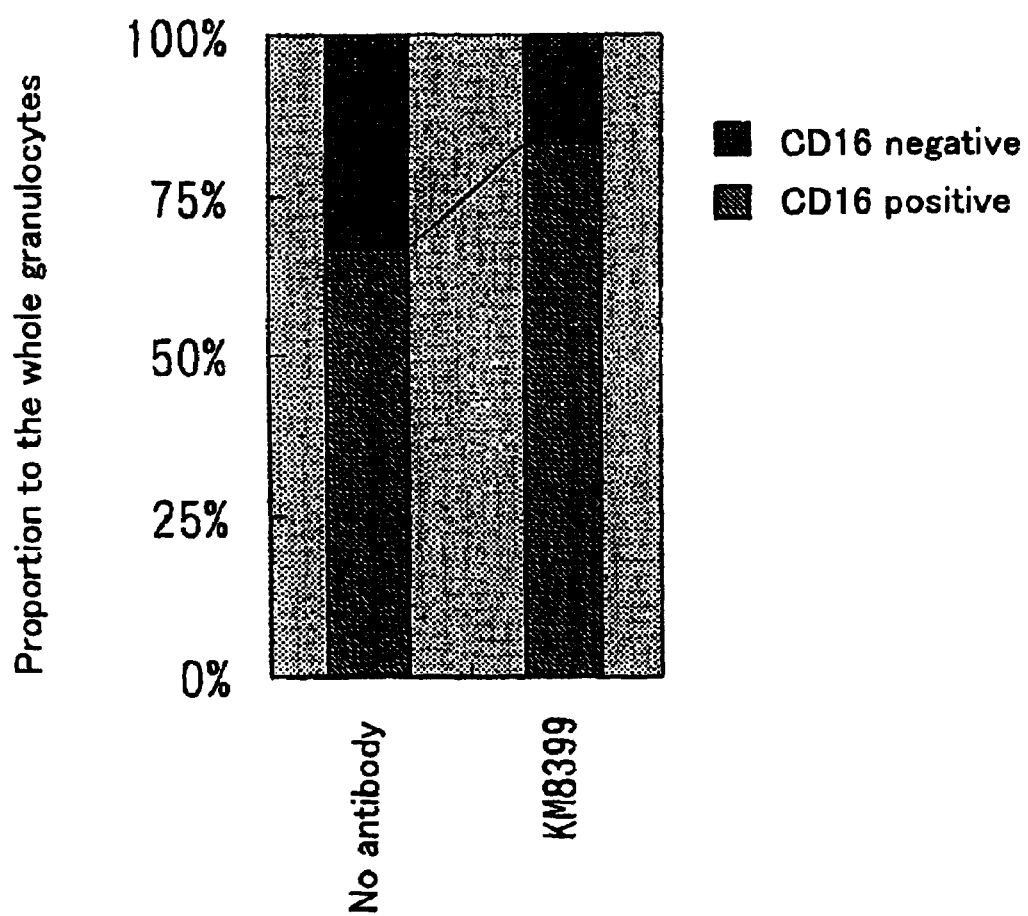
FIG. 10 shows the increasement of CD16 positive cells after incubation with KM8399. The vertical axis indicates the percentage of CD16 positive cells in the granulocytes, and the horizontal axis indicates antibody.

Lymphocytes and granulocytes were fractionated by the method of Example 1, and 50 μl of the fraction ($5 \times 10^5$ cells) was apportioned to each well of a 96-well U-shaped plate. Then, KM8399 previously prepared at 2 μg/ml with 10% FCS-RPMI was apportioned at 100 μl/well to the plate, and then cultured under the air containing 5% $CO_2$ at 37° C. for 96 hours. After culturing, cells were centrifuged at 350×g for 3 minutes at 4° C. to remove the supernatant. The cells were washed by adding 100 μl of a buffer for measurement [PBS (phosphate-buffered saline) containing 1% bovine serum albumin, 0.02% EDTA (ethylenediamine-N,N,N'N'-tetraacetic acid), 0.05% sodium azide] to each well. Then, FITC-labeled anti-CD16 antibody (Nippon Becton Dickinson Company, Ltd.) was added at 20 μl/well for reaction to proceed on ice for 30 minutes. Then, the reaction product was washed by centrifugation with a buffer for measurement in triplicate, and then the fluorescence intensity of FITC was measured with a flow cytometer. The results are shown in FIG. 10.

In the group added with KM8399, CD16 negative eosinophils decreased and CD 16 positive neutrophils increased, compared to the group to which no antibody was added.

EXAMPLE 7

Detection of Apoptosis of Activated Eosinophils

The apoptosis detection method of 3 (1) mentioned above was improved, and then apoptosis of activated eosinophils was detected by the improved method. 100 μl of eosinophils ($4 \times 10^5$ cells/ml) and of PBMC ($1 \times 10^6$ cells/ml) isolated from peripheral blood were together added to each well of a 96-well plate, followed by co-culturing for 48 hours to induce activated eosinophils. The thus co-cultured eosinophils expressed CD69 molecules, the activated eosinophil marker.

After co-culturing, 100 μl of the culture supernatant was removed from each well, and then 100 μl of various antibody diluents (2 μg/ml) was added respectively (final concentration 1 μg/ml), followed by another culturing for 20 hours. After culturing, apoptotic cells were detected by staining with annexin V-FITC.

Figure 11:
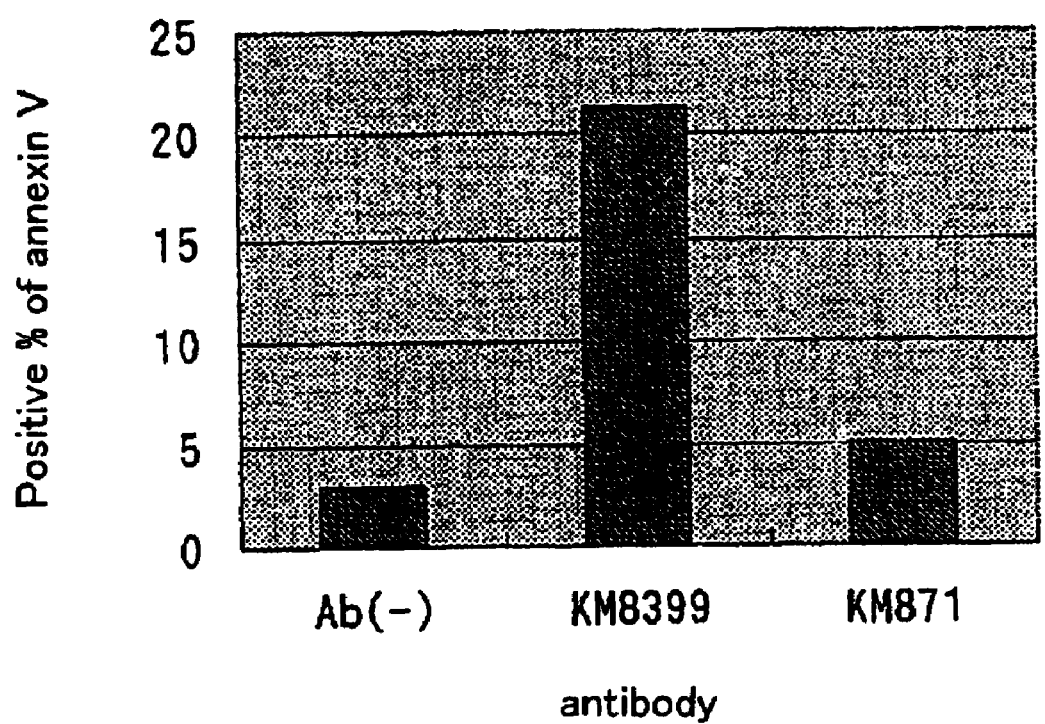
FIG. 11 shows the apoptosis-inducing activity on activated eosinophils. The vertical axis indicates the positive % of annexin V, and the horizontal axis indicates antibody.

As shown in FIG. 11, KM8399 significantly induced apoptosis of activated eosinophils. Inhibiting IL-5 only cannot remove nor reduce activated eosinophils, because activated eosinophils survive in the absence of cytokines. These results suggest that KM8399 can remove or reduce not only eosinophils in peripheral blood, but also activated eosinophils infiltrating inflammated areas, and that KM8399 is clinically useful.

INDUSTRIAL APPLICABILITY

The apoptosis inducer of the present invention is useful in treating inflammatory disorders, such as chronic bronchial asthma, eosinophilic diseases, such as eosinophilic granuloma, or the like, by inducing eosinophil apoptosis to reduce or remove eosinophils or activated eosinophils.

The invention claimed is:

1. A method for specifically inducing apoptosis of an eosinophil, comprising:
    administering an anti-human interleukin-5 receptor α-chain monoclonal antibody with an Fc region of the human IgG1 subclass that has antibody-dependent cellular cytotoxicity to a patient in need thereof in an amount effective to induce apoptosis of an eosinophil in said patient.

2. The method of claim 1, wherein the anti-human interleukin-5 receptor α-chain monoclonal antibody is produced by an animal cell.

3. The method of claim 1, wherein the anti-human interleukin-5 receptor α-chain monoclonal antibody is produced by the transformant KM8399 (FERM BP-5648).

4. A method for specifically reducing or removing eosinophils in peripheral blood or in tissues infiltrated with eosinophils, compnsing:
    administering an anti-human interleukin-5 receptor α-chain monoclonal antibody with an Fc region of the human IgG1 subclass that has antibody-dependent cellular cytotoxicity to a patient in need thereof in an amount effective to remove or reduce said eosinophils.

5. The method of claim 4, wherein the anti-human interleukin-5 receptor α-chain monoclonal antibody is produced by an animal cell.

6. The method of claim 4, wherein the anti-human interleukin-5 receptor α-chain monoclonal antibody is produced by the transformant KM8399 (FERM BP-5648).

7. The method of claim 1, wherein inducing apoptosis of said eosinophil treats chronic bronchial asthma, atopic dermatitis, eosinophilia, eosinophilic enterogastritis, eosinophilic leukemia, eosinophilic granuloma or Kimura's disease in a patient in need thereof.

8. The method of claim 2, wherein inducing apoptosis of said eosinophil treats chronic bronchial asthma, atopic dermatitis, eosinophilia, eosinophilic enterogastritis, eosinophilic leukemia, eosinophilic granuloma or Kimura's disease in a patient in need thereof.

9. The method of claim 3, wherein inducing apoptosis of said eosinophil treats chronic bronchial asthma, atopic dermatitis, eosinophilia, eosinophilic enterogastritis, eosinophilic leukemia, eosinophilic granuloma or Kimura's disease in a patient in need thereof.

10. The method of claim 4, wherein removing or reducing said eosinophils treats chronic bronchial asthma, atopic dermatitis, eosinophilia, eosinophilic enterogastritis, eosinophilic leukemia, eosinophilic granuloma or Kimura's disease in a patient in need thereof.

11. The method of claim 5, wherein removing or reducing said eosinophils treats chronic bronchial asthma, atopic dermatitis, eosinophilia, eosinophilic enterogastritis, eosinophilic leukemia, eosinophilic granuloma or Kimura's disease in a patient in need thereof.

12. The method of claim 6, wherein removing or reducing said eosinophils treats chronic bronchial asthma, atopic dermatitis, eosinophilia, eosinophilic enterogastritis, eosinophilic leukemia, eosinophilic granuloma or Kimura's disease in a patient in need thereof.

* * * * *

UNITED STATES PATENT AND TRADEMARK OFFICE
CERTIFICATE OF CORRECTION

PATENT NO. : 7,404,953 B2
APPLICATION NO. : 10/204326
DATED : July 29, 2008
INVENTOR(S) : Emi Hosaka et al.

It is certified that error appears in the above-identified patent and that said Letters Patent is hereby corrected as shown below:

<u>COLUMN 1</u>

Line 35, "cosinophulia" should read --eosinophilia--.

<u>COLUMN 7</u>

Line 28, "an" should be deleted; and
Line 36, "sesami" should read --sesame--.

<u>COLUMN 14</u>

Line 47, "compnsing:" should read --comprising:--.

Signed and Sealed this

Second Day of December, 2008

JON W. DUDAS
*Director of the United States Patent and Trademark Office*